United States Patent
Elliott et al.

(10) Patent No.: US 7,019,138 B2
(45) Date of Patent: Mar. 28, 2006

(54) METAL COMPLEX-BASED ELECTRON-TRANSFER MEDIATORS IN DYE-SENSITIZED SOLAR CELLS

(75) Inventors: C. Michael Elliott, Fort Collins, CO (US); Shawn A. Sapp, Broomfield, CO (US); Carlo Alberto Bignozzi, Ferrara (IT); Cristiano Contado, Legnago (IT); Stefano Caramori, Viconovo (IT)

(73) Assignees: Colorado State University Research Foundation, Fort Collins, CO (US); The University of Ferrara, Ferrara (IT)

( * ) Notice: Subject to any disclaimer, the term of this patent is extended or adjusted under 35 U.S.C. 154(b) by 0 days.

(21) Appl. No.: 10/494,086

(22) PCT Filed: Oct. 30, 2002

(86) PCT No.: PCT/US02/34883

§ 371 (c)(1),
(2), (4) Date: Aug. 18, 2004

(87) PCT Pub. No.: WO03/038508

PCT Pub. Date: May 8, 2003

(65) Prior Publication Data

US 2004/0267018 A1 Dec. 30, 2004

Related U.S. Application Data

(60) Provisional application No. 60/335,942, filed on Oct. 30, 2001.

(51) Int. Cl.
- C07F 15/00 (2006.01)
- G02F 1/15 (2006.01)
- G02B 5/23 (2006.01)
- H01M 6/30 (2006.01)

(52) U.S. Cl. ............... 546/2; 556/136; 556/141; 429/111; 359/265; 252/586

(58) Field of Classification Search ............... 556/138, 556/141; 546/2; 136/243; 359/265; 429/111; 252/586

See application file for complete search history.

(56) References Cited

U.S. PATENT DOCUMENTS

| | | | | |
|---|---|---|---|---|
| 5,350,644 | A | * | 9/1994 | Graetzel et al. ............ 429/111 |
| 6,150,605 | A | * | 11/2000 | Han ............................ 136/263 |
| 6,734,305 | B1 | * | 5/2004 | Pierre et al. ................ 544/347 |

OTHER PUBLICATIONS

Chen, Y. D. et al., Journal of the Electrochemical Society, Jan. 1982, vol. 129, No. 1, pp. 61-66.*
Rao et al., Inorganica Chimica Acta, vol. 41, pp. 221-226 (1980).*

(Continued)

Primary Examiner—Porfirio Nazario-Gonzalez
(74) Attorney, Agent, or Firm—Faegre & Benson LLP

(57) ABSTRACT

This present invention provides a metal-ligand complex and methods for using and preparing the same. In particular, the metal-ligand complex of the present invention is of the formula:

$$L_a\text{-}M\text{-}X_b$$

where L, M, X, a, and b are those define herein. The metal-ligand complexes of the present invention are useful in a variety of applications including as electron-transfer mediators in dye-sensitized solar cells and related photo-electrochromic devices.

28 Claims, 6 Drawing Sheets

R = ethyl (te-terpy)
R = t-butyl (ttb-terpy)
R' = H, R" = H (bpy)
R' = CH₃, R" = H (4,4'-dmb)
R' = H, R" = CH₃ (5,5'-dmb)
R' = CH₃, R" = CH₃ (tm-bpy)
R' = (amide group), R" = H (bdb-amd)

R' = t-butyl, R" = H (dtb-bpy)
R' = COO-t-butyl, R" = H (dtb-est)
R' = phenyl, R" = H (dp-bpy)
R' = 3-pentyl, R" = H (d3p-bpy)
R' = nonyl, R" = H (dn-bpy)
X = H (phen)
X = phenyl (phen-phen)

OTHER PUBLICATIONS

C. Wen et al., "Effects of Silver Particles on the Photovoltaic Properties of Dye-Sensitized $TiO_2$ Thin Films," Solar Energy Materials & Solar Cells, vol. 61, (2000) pp. 339-351.

Pierre Bonhote et al., "Redox Mediators for Electrochemical Photovoltaic Cells Based on Dye-Sensitized $TiO_2$ Electrodes," presented at the 10$^{th}$ International Conference on Photochemical Conversion and Storage of Solar Energy (IPS-10), Interlaken, Switzerland, (1994) Abstract C2.

Shawn A. Sapp et al., "Substituted Polypridine Comlplexes of Cobalt(II/III) as Efficient Electron-Transfer Mediators in Dye-Sensitized Solar Cells," J. Am. Chem. Soc. (2002), vol. 124, No. 37, pp. 11215-11222.

* cited by examiner

R = ethyl (te-terpy)

R = *t*-butyl (ttb-terpy)

R' = H, R" = H (bpy)

R' = CH$_3$, R" = H (4,4'-dmb)

R' = H, R" = CH$_3$ (5,5'-dmb)

R' = CH$_3$, R" = CH$_3$ (tm-bpy)

R' =  , R" = H (bdb-amd)

R' = *t*-butyl, R" = H (dtb-bpy)

R' = COO-*t*-butyl, R" = H (dtb-est)

R' = phenyl, R" = H (dp-bpy)

R' = 3-pentyl, R" = H (d3p-bpy)

R' = nonyl, R" = H (dn-bpy)

X = H (phen)

X = phenyl (phen-phen)

METAL COMPLEX-BASED ELECTRON-TRANSFER MEDIATORS IN DYE-SENSITIZED SOLAR CELLS

CROSS-REFERENCES TO RELATED APPLICATIONS

This application claims the benefit of priority of PCT/US02/34883, filed Oct. 30, 2002, now International Publication No. WO 2003/038508, dated May 8, 2003, which claims the priority benefit of U.S. Provisional Patent Application No. 60/335,942, filed Oct. 30, 2001, both of which are incorporated herein by reference in their entirety.

STATEMENT REGARDING FEDERALLY FUNDED RESEARCH

The U.S. Government has paid-up license in this invention and the right in limited circumstances to require the patent owner to license others on reasonable terms as provided for by the terms of Grant No. DE-FG03-97ER14808 awarded by the U.S. Department of Energy, and Grant Nos. CHE-0139637 and CHE-9714081 awarded by the National Science Foundation.

FIELD OF INVENTION

This present invention relates to a metal-ligand complex of the formula $L_a$-M-$X_b$ and methods for using and preparing the same. In particular, metal-ligand comlpexes of the present invention are useful as electron-transfer mediators in dye-sensitized solar cells and related photoelectrochromic devices.

BACKGROUND OF THE INVENTION

The spectral characteristics of wide-bandgap semiconductors have been enhanced through the use of adsorbed dye molecules. This is referred to as dye sensitization, and cells incorporating these materials as photoanodes are described as dye-sensitized solar cells (hereafter DSSC's). See, for example, A. Hagfeldt and M. Graetzel, *Acc. Chem. Res.*, 2000, 33, p. 269–277, which is incorporated herein by reference in its entirety. As a whole, DSSC's are composed of three basic components: the photoanode, the electron-transfer mediator, and the cathode. A rather large variety of semiconductors and dyes are known to yield effective photoanodes. There are, however, a limited number of known electron-transfer mediators and compatible cathode materials that produce effective solar cells when combined with a known photoanode. See, for example, Lenzmann, et al., *J. Phys. Chem. B*, 2001, 105, 6352; Magnisson et al., *Solar Energy Materials and Solar Cells*, 2002, 73, 51–58; and Turkovic et al., *Solar Energy Materials and Solar Cells*, 1997, 45, 275–281, all of which are incorporated herein by reference in their entirety.

Iodide salts of inorganic and organic cations when mixed with iodine (hereinafter $I^-/I_3^-$) at varying ratios and concentrations in aprotic solvents are known to be effective electron-transfer mediators in DSSC's. See, for example, Nazeeruddin et al., *J. Am. Chem. Soc.*, 1993, 115, p. 6382–90. Comparable bromide salts mixed with bromine (hereafter $Br^-/Br_2$) are less effective and less preferred, but are also known. See, for example, Heimer et al., *J. Phys. Chem.*, 1993, 97, p. 11987–94; and Vlachopoulos et al., *J. Am. Chem. Soc.*, 1988, 110, p. 1216–20. With both the $I^-/I_3^-$ and the $Br^-/Br_2$ mediators, there are a number of drawbacks. Often cell construction is complicated by issues of chemical compatibility with the electron-transfer mediator. Both the $I^-/I_3^-$ and $Br^-/Br_2$ mediator mixtures are highly corrosive. With a few exceptions, notably titanium or platinum, the use of metals must be avoided for successful long-term operation of the cells. The volatility of both iodine and bromine further complicates the sealing of cells, and leakage is often the cause of device failure.

There has also been a report of a cobalt complex-based mediator that rivaled the $I^-/I_3^-$ mediator in terms of the kinetics to regenerate the dye. Nusbaumer et al., *J. Phys. Chem. B*, 2001, 105, 10461. However, the ligands used to form this complex are not readily available, and are believed to require a multi-step synthetic procedure, thereby adding time and cost in producing these electron-transfer mediators. Many other previous efforts in cobalt complexes as mediators in DSSCs have also been not too successful. See, for example, Bonhote et al., *Presented at the 10th International Conference on Photochemical Conversion and Storage of Solar Energy (IPS-10)*, Interlaken, Switzerland, 1994, Abstract C2; and Wen et al., *Sol. Energy Mater. Sol. Cells*, 2000, 61, 339.

Platinum and titanium are known to be compatible cathode materials, being resistant to the corrosive nature of the above electron-transfer mediators. Platinum is generally most preferred because its surface is known to be catalytic for the reduction of iodine to iodide. Gold, silver, nickel, iron, chromium, aluminum, and copper (along with most other metals and alloys thereof) cannot be used with $I^-/I_3^-$. This limitation has been one of the major obstacles in the commercialization of DSSC's.

Passivation with electrically insulating materials of one or more of the active surfaces in the photoanode is known to allow the use of other electron-transfer mediators such as ferrocene/ferrocenium. See, for example, Gregg et al., *J. Phys. Chem. B*, 2001, 105, p. 1422–1429. However, the performance of these cells does not approach that of cells using $I^-/I_3^-$. Additionally, the passivation methods are known to be difficult to control and reproduce.

The operation of the dye-sensitized photoanode in certain photoelectrochromic devices is subject to most of the same considerations as DSSC's. See, for example, Pichot et al., *J. Electrochem. Soc.*, 1999, 146, p. 4324–4326, which is incorporated herein by reference in its entirety. Consequently, similar advantages will be accrued by replacing the $I^-/I_3^-$ electron-transfer mediator system with the present invention in photoelectrochromic devices.

Therefore, there is a need for other simple and efficient electron-transfer mediators.

SUMMARY OF THE INVENTION

One aspect of the present invention provides a metal-ligand complex of the formula:

$$L_a\text{-M-}X_b \qquad \qquad \text{I}$$

wherein a is an integer from 1 to 6; b is an integer from 0 to 5, provided the sum of a and b equal the appropriate total number of ligands present on the metal M; M is a transition metal; each X is independently a co-ligand; and each L is independently a polypyridine ligand.

The present invention also provides methods for using and making compounds of Formula I above. In one particular embodiment, the present invention provides an electron-transfer mediator comprising the metal-ligand complex of Formula I above.

DETAILED DESCRIPTION OF THE INVENTION

Definitions

Figure 1:
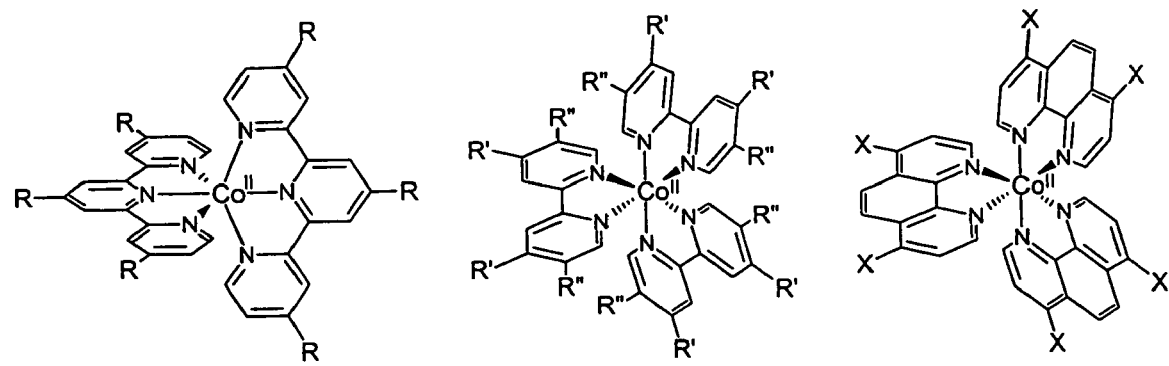
FIG. 1 shows some of the representative electron-transfer mediators of the present invention which comprises a series of terpyridine, bipyridine, and phenanthroline complexes of cobalt(II). The abbreviated names, as used in the text, refer to the entire complex, not the ligands.
Figure 1:
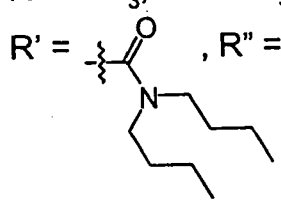

The term "alkyl" refers to a linear or branched saturated monovalent hydrocarbon moiety, preferably having from one to about 12 carbon atoms. Exemplary alkyl groups include methyl, ethyl, n-propyl, 2-propyl, tert-butyl, pentyl, 3-pentyl, hexyl, heptyl, octyl, nonyl, and the like.

The term "alkylene" refers to a linear or branched saturated divalent hydrocarbon moiety, preferably having from one to about 12 carbon atoms. Exemplary alkylene groups include methylene, ethylene, n-propylene, 2-propylene, tert-butylene, pentylene, 3-pentylene, hexylene, heptylene, octylene, nonylene, and the like.

The term "aryl" refers to a monovalent aromatic hydrocarbon ring moiety, such as mono-, bi- or tri-cyclic aromatic carbocyclic ring moieties. Exemplary aryls include, but are not limited to, phenyl and naphthyl. Aryl groups can optionally be substituted with one or more substituents such as alkyl, halo, hydroxyl, or alkoxy.

The term "aralkyl" refers to a moiety of the formula —R'R", where R' is alkylene and R" is aryl as defined herein.

The term "carboxy" refers to a moiety of the formula —C(=O)—OR$^a$, where R$^a$ is hydrogen, alkyl, cycloalkyl, haloalkyl, aryl, or aralkyl. Preferably R$^a$ is alkyl. And the term "alkyl carboxy" refers to a carboxy moiety as defined herein where R$^a$ is alkyl.

The term "carboxylate" refers to a moiety of the formula —OC(=O)R$^z$, where R$^z$ is hydrogen, alkyl, cycloalkyl, aryl, or aralkyl.

The term "cycloalkyl" refers to a mono- or bicyclic saturated monovalent hydrocarbon moiety, preferably having from three to about 12 carbon atoms. Exemplary cycloalkyl groups include cyclopropyl, cyclobutyl, cyclopentyl, cyclohexyl, cycloheptyl, cyclooctyl, cyclododecyl, bicyclo[4.4.0]decyl, and the like.

The term "amide" refers to a moiety of the formula —C(=O)—NR$^b$R$^c$, where each of R$^b$ and R$^c$ is independently, hydrogen, alkyl, cycloalkyl, haloalkyl, aryl, or aralkyl. Preferably, R$^b$ and R$^c$ are independently hydrogen or alkyl.

The term "haloalkyl" refers to an alkyl group in which one or more hydrogen atom has been replaced by halide. Exemplary haloalkyl groups include —CH$_2$Cl, —CF$_3$, —CH$_2$CF$_3$, —CH$_2$CCl$_3$, and the like, and further includes those alkyl groups such as perfluoroalkyl in which all alkyl hydrogen atoms are replaced by fluorine atoms.

The term "polypyridine" refers to a moiety comprising two or more pyridine ring system which are covalently linked to one another. Each of the covalently linked pyridine ring system can optionally be substituted with alkyl, halo, haloalkyl, carboxy, amide, or aryl. In addition, the covalently linked pyridine ring systems can together form a larger ring system. Preferred polypyridines include bipyridine, terpyridine, phenanthroline, and the derivatives thereof.

The terms "bidentate polypyridine", "tridentate polypyridine", and "tetradentate polypyridine" refer to a polypyridine moiety having two, three, and four pyridine nitrogen atoms, respectively, which are coordinated to the metal.

As used herein, the terms "those defined above" and "those defined herein" when referring to a variable incorporates by reference the broad definition of the variable as well as preferred, more preferred and most preferred definitions, if any.

Compounds of the Present Invention

The present invention provides a metal-ligand complex comprising a moiety of the formula:

$$L_a\text{-}M\text{-}X_b \qquad \text{(Formula I)}$$

where M is a transition metal, preferably cobalt, and more preferably cobalt having oxidation state of 2 or 3; a is an integer from 1 to 6, preferably 2 or 3; b is an integer from 0 to 5, preferably 0; each X is independently a co-ligand; and each L is independently a polypyridine ligand, provided that the sum of a and b equal the appropriate total number of ligands present on the metal M. For example, when M contains a total of six ligand binding sites and L is a bidentate ligand, then the sum of 2a+b is 6, and when M contains four ligand binding sites and L is a tridentate ligand, then 3a+b is 4, i.e., a and b are 1.

Preferably, each L is independently a bidentate, a tridentate or a tetradentate polypyridine ligand. More preferably, each L is independently a bidentate or a tridentate polypyridine ligand. Still more preferably, each L is independently terpyridine, bipyridine, or phenanthroline, each of which is optionally substituted. In one embodiment, L comprises at least one substituent which has a steric volume larger than a methyl group.

Preferably, the tridentate polypyridine ligand is optionally substituted terpyridine. More preferably, the tridentate polypyridine is of the formula:

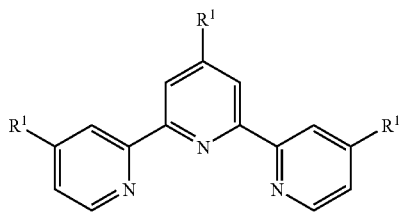

Formula II where each $R^1$ is independently hydrogen, alkyl, cycloalkyl, aryl, haloalkyl, heteroaryl, carboxy, or amide. Preferably, each $R^1$ is independently hydrogen, alkyl, or haloalkyl. More preferably, each $R^1$ is independently hydrogen or alkyl. Still more preferably, at least one $R^1$ is alkyl. And more preferably, each $R^1$ is alkyl. Still yet more preferably, each $R^1$ is independently selected from the group consisting of ethyl and tert-butyl. In one specific embodiment, $R^1$ is ethyl. In another specific embodiment, $R^1$ is tert-butyl.

Preferably, the bidentate polypyridine ligand is optionally substituted bipyridine or optionally substituted phenanthroline. More preferably, the bidentate polypyrdine is of the formula:

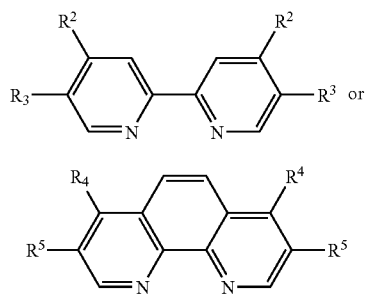

Formula III

Formula IV where each of $R^2$, $R^3$, $R^4$, and $R^5$ is independently hydrogen, alkyl, aryl, carboxy, amide, cycloalkyl, haloalkyl, or heteroaryl.

Preferably, each $R^2$ is independently selected from the group consisting of hydrogen, alkyl, aryl, carboxy, and amide. More preferably, each $R^2$ is independently selected from the group consisting of hydrogen, alkyl, N,N-dialkyl amide, alkyl carboxy, and phenyl. Still more preferably, each $R^2$ is independently selected from the group consisting of hydrogen, methyl, tert-butyl, 3-pentyl, nonyl, N,N-dibutyl amide, tert-butyl carboxy, and phenyl.

Preferably, each $R^3$ is independently selected from the group consisting of hydrogen, alkyl, aryl, carboxy, and amide. More preferably, each $R^3$ is independently hydrogen or alkyl. Still more preferably, each $R^3$ is independently hydrogen or methyl.

Preferably, each $R^4$ is independently selected from the group consisting of hydrogen, alkyl, aryl, carboxy, and amide. More preferably, each $R^4$ is independently hydrogen or aryl. Yet more preferably, each $R^4$ is independently hydrogen or optionally substituted phenyl. Still more preferably, each $R^4$ is independently hydrogen or phenyl.

Preferably, each $R^5$ is independently selected from the group consisting of hydrogen, alkyl or haloalkyl. More preferably, each $R^5$ is independently hydrogen or alkyl. Still more preferably, $R^5$ is hydrogen.

Still more preferably, at least one of the substituents of the polypyridine ligand of Formulas II, III, and IV is a substituent other than hydrogen or methyl. And more preferably, at least one of the substituents of the polypyridine ligand of Formulas II, III, and IV is a substituent having a steric volume greater than a methyl group.

It is to be understood that the scope of this invention encompasses not only the various polypyridine ligand isomers which may exist but also the various mixture of polypyridine ligand isomers which may be formed depending on the substituents that are present on the polypyridine ligand.

In particular, if the metal-ligand complex of the present invention contains one or more chiral centers, the metal-ligand complex can be synthesized enantioselectively or a mixture of enantiomers and/or diastereomers can be used as is or prepared and separated. The resolution of the compounds of the present invention, their starting materials and/or the intermediates can be carried out by any of the methods known to one skilled in the art. See for example, *Optical Resolution Procedures for Chemical Compounds*: Optical Resolution Information Center, Manhattan College, Riverdale, N.Y., and in *Enantiomers, Racemates and Resolutions*, Jean Jacques, Andre Collet and Samuel H. Wilen; John Wiley & Sons, Inc., New York, 1981, which are incorporated herein in their entirety. Basically, the resolution of the compounds is based on the differences in the physical properties of diastereomers by attachment, either chemically or enzymatically, of an enantiomerically pure moiety results in forms that are separable by fractional crystallization, distillation or chromatography.

When one or more co-ligand is present in the metal-ligand complex, each co-ligand, X, is independently selected from a conventional transition metal ligands known to one skilled in the art. Exemplary co-ligands include halide, alkyl, carboxylate, nitro, nitroso, a phosphine derivative (such as triarylphosphine, trialkylphosphine, etc.), and the like.

Still further, combinations of the preferred groups described herein form other preferred embodiments. For example, in one particularly preferred embodiment M is cobalt, L is terpyridine of formula II and $R^1$ is tert-butyl. In this manner, a variety of preferred compounds are embodied within the present invention.

It should be appreciated that when the metal, M, is not a neutral species, the metal-ligand complex constitutes only a partial representation of a chemical compound. Indeed, in an isolable compound, such a moiety must be paired with a counterion (e.g., anion or cation) that is necessary to maintain electroneutrality. Thus, compounds of the present invention are, more accurately, represented by the formula:

$$[(L)_a\text{-}M\text{-}(X)_b]_m Y_n \qquad \text{(Formula IA)}$$

where L, M, X, a and b are those defined above, Y is a counterion and the variables m and n are oxidation state of the counterion and the metal-ligand complex, respectively, with a proviso that when the metal-ligand complex is not charged no counterion will be present and n=0 and m is 1. While Y can sometimes affect the solubility or other nonelectrochemical property of the metal-ligand complex, the exact nature of Y is not critical.

Preferred compatible anions, i.e., Y, are: $ClO_4^-$, $BF_4^-$, $PF_6^-$, p-toluenesulfonate$^-$, $NO_3^-$ and trifluoromethanesulfonate. With $ClO_4^-$ anion being a preferred counter anion. Preferred compatible cations, i.e., Y, are: $Li^+$, $Na^+$, $K^+$, $NH_4^+$ and $NR_4^+$ where R is a straight chain alkane containing 1 through 8 carbons. However, the present invention is not limited to these counterions.

If desired, a counter-ion associated with a metal-ligand complex cation (or anion) can be readily exchanged with another counter-ion by any of the methods known to one skilled in the art, including ion exchange chromatography and other ion exchange methods.

Synthesis

The metal-ligand complex of the present invention can be synthesized from readily available starting materials. Typically, a polypyridine compound is dissolved in an organic solvent and an appropriate amount of metal salt is added. The mixture is then stirred at a temperature and for a period sufficient to affect exchange of ligands to produce the desired metal-ligand complex. The reaction temperature can range from room temperature to the boiling point of the solvent used.

Typically, the ligand exchange reaction is carried out by refluxing the mixture. Suitable reaction solvents include alcohols (e.g., methanol, ethanol, isopropanol, etc.), and other solvents well known to one skilled in the art.

The reaction time can vary depending on a variety of factors, including the polypyridine compound and the metal salt used. Other factors include reaction solvent, reaction temperature, and concentrations of each reaction components. The reaction time generally ranges from few minutes to few hours. Typically, the reaction time ranges from 1 to 5 hours.

The reaction conditions are not limited to those described above and examples given herein. The reaction conditions can vary depending on the particular reaction solvent, polypyridine, and metal salt used in order to affect the desired ligand exchange reaction.

Various polypyridine ligand compounds are commercially available or can be readily obtained from commercially available starting materials. Thus, various substituents on the polypyridine ligand of the present invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in *Protective Groups in Organic Synthesis*, 3rd edition, T. W. Greene and P. G. M. Wuts, John Wiley & Sons, New York, 1999, which is incorporated herein by reference in its entirety. For example, nitro groups can be added to an aromatic ring system by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

Since the compounds of the present invention can have certain substituents which are necessarily present, the introduction of each substituent is, of course, dependent on the specific substituents involved and the chemistry necessary for their formation. Thus, consideration of how one substituent would be affected by a chemical reaction when forming a second substituent would involve techniques familiar to one of ordinary skill in the art. This would further be dependent on the nature of the polypyridine involved.

Utility

Certain photoelectrochemical cells based on dye-sensitized nanocrystalline $TiO_2$ photoanodes can have total energy conversion efficiency in excess of 10% when irradiated with sunlight. See, for example, Nazeeruddin et al., *J. Am. Chem. Soc.*, 2001, 123, 1613. Such efficiencies meet or exceed those of solid-state cells based on amorphous silicon but fall far short of the efficiency of single crystal and poly-crystalline silicon cells. Green, *MRS Bull.*, 1993, 18, 26; Watanabe, *MRS Bull.*, 1993, 18, 29; and Hamakawa et al., *MRS Bull.*, 1993, 18, 38. That fact notwithstanding, the potential for fabricating large surface area cells out of relatively inexpensive materials—compared to single crystalline silicon cells, for example—is driving interest in dye-sensitized solar cells (DSSCs).

While the demonstrated energy conversion efficiencies of DSSCs have become competitive with some existing commercial technologies, there are a number of issues that remain to be addressed before this type of cell can become truly commercially viable. Currently, the best "dyes" for sensitizing the $TiO_2$ photoanode are ruthenium-based coordination complexes. With such dyes there are potential stability issues. Furthermore, ruthenium is relatively rare. To date, only cells based on liquid-state electrolytes have produced the high efficiencies required for competitiveness with existing technologies. Cao et al., *J. Phys. Chem.*, 1995, 99, 17071; Papageorgiou et al., *J. Electrochem. Soc.*, 1996, 143, 3099; Murakoshi et al., *Chem. Lett.*, 1997, 471; Murakoshi et al., *Sol. Energy Mater. Sol. Cells*, 1998, 55, 113; and Savenije et al., *Chem. Phys. Lett.*, 1998, 287, 148. Unfortunately, an extremely limited set of electron-transfer mediators work in these cells. The overall best system to date is the $I^-/I_3^-$ couple, which has a list of undesirable chemical properties. Gregg et al., *J. Phys. Chem. B*, 2001, 105, 1422.

Considerable effort has been focused on finding new dyes. Hagfeldt et al., *Acc. Chem. Res.*, 2000, 33, 269. In contrast, efforts to find electron-transfer mediators other than $I^-/I_3^-$ have been relatively modest. Gregg et al., *J. Phys. Chem. B*, 2001, 105, 1422; and Oskam et al., *J. Phys. Chem. B*, 2001, 105, 6867. The $I^-/I_3^-$ couple functions well in these cells because of a fortunate confluence of the right kinetics for at least four different heterogeneous electron-transfer reactions: (1) The photo-excited dye must inject an $e^-$ faster than it reacts with the mediator. (2) The oxidized dye must be reduced by the mediator more rapidly than it recombines with the photoinjected electron. (3) The oxidized mediator must, itself, react slowly with electrons in both the $TiO_2$ and the fluorine-doped tin oxide ($SnO_2$:F) contact. (4) Finally, the reduction of the oxidized mediator at the cathode must be rapid.

Present inventors have discovered that metal-ligand complexes of the present invention—some of which are formed from structurally simple ligands—function as efficient electron-transfer mediators in DSSCs. FIG. 1 shows a representative metal-ligand complexes of the present invention.

When metal-ligand complexes of the present invention are used as electron-transfer mediators, efficiencies of such electron-transfer is at least about 50%, preferably at least about 70% and more preferably greater than 80%, of that given by the comparable cell mediated by the $I^-/I_3^-$ couple.

Thus, metal-ligand complexes of the present invention are useful in a variety of application, including as electron-transfer mediators, especially in dye-sensitized solar cells (e.g., batteries) and related photoelectrochromic devices. As stated above, conventional solar cells typically utilize $I^-/I_3^-$ system as an electron-transfer mediator. Unfortunately, $I^-/I_3^-$ system is corrosive and $I_2$ which is a component of the $I^-/I_3^-$ system is volatile.

In contrast, metal-ligand complexes of the present invention are significantly less corrosive than the $I^-/I_3^-$ system and significantly less volatile than $I_2$. Thus, use of non-volatile and non-corrosive metal-ligand complexes of the present invention enable the facile fabrication of solar cells, including solar cells containing cathodes of materials other than platinum or titanium, and allows for long-term stability in sealed cells.

The electron-transfer mediators of the present invention are redox-active metal complexes. Such electron-transfer mediators can be used in conjunction with or in place of other conventional electron-transfer mediators, including $I^-/I_3^-$ system.

Typically, when simple outer-sphere type redox agents are used as electron-transfer mediators in DSSC's (in place of $I^-/I_3^-$), the rate of heterogeneous electron transfer between the oxidized form of the mediator molecule and either the semiconductor particle surface or the surface of the electrical contact to the semiconductor-particle film, or both (i.e., "undesired reactions"), is significantly faster than the rates of mass transfer of the oxidized mediator to the cathode or the heterogeneous reduction of the oxidized mediator at the cathode (i.e., "desired reactions"). As a result of these undesired reactions, the photocurrents generated by cells employing such mediators are small and their light-to-electrical-energy conversion efficiencies are poor when compared to identical cells employing $I^-/I_3^-$ as the electron-transfer mediator.

In contrast, without being bound to any theory, it is believed that the metal-ligand complexes of the present invention have built into their structure a means or multiple means to significantly reduce the rates of these undesired surface reactions. This reduction in undesired reaction rate is typically accomplished without any special chemical or physical treatment of the semiconductor or electrical contact surfaces that might also serve to slow the undesired reverse electron transfer reactions. It is believed that the desired redox reactions of these complexes with the oxidized dye on the semiconductor surface and the cathode remain fast enough for the cell to function with reasonable efficiencies. Thus, highly efficient solar cells are obtained by using a metal-ligand complex of the present invention.

Electron-transfer mediator systems comprising a metal-ligand complex of the present invention function efficiently under a wider range of solvent conditions. Furthermore, since metal-ligand complexes of the present invention are significantly less corrosive than $I^-/I_3^-$ system, they are compatible with a wider range of potential electrode materials than $I^-/I_3^-$ system. In addition, a relatively non-corrosive property allows metal-ligand complex of the present invention to be used as an electron-transfer mediator system that is compatible with a wide variety of potential structural materials, such as metals, plastics and other polymers known to one skilled in the art. Moreover, due to its relatively non-volatile nature, metal-ligand complexes of the present invention can be used as electron-transfer mediator systems in gel electrolytes, in the solid state, or in polymeric form.

In application as an electron-transfer mediator in DSSC's, the preferred use is a combination of the two oxidation-state forms of the complex with otherwise the same structure. The most preferred combination is 10% n=3 and 90% n=2, where the percentages refer to the relative amounts of each oxidation-state form of the metal-ligand complex.

EXAMPLES

The following examples are offered to illustrate, but not to limit the claimed invention.

Materials. Acetonitrile (Fisher Optima Grade), anhydrous ethanol (Pharmco), and all other solvents (Fisher ACS Grade) were used as received. Cobalt(II) perchlorate hexahydrate, 10% palladium on activated carbon, γ-butyrolactone, thionyl chloride, t-butyl alcohol, dibutylamine, 4-t-butylpyridine, 2,2'-dipyridyl, 4,4'-diphenyl-2,2'-dipyridyl, 4,4'-di-t-butyl-2,2'-dipyridyl, 4,4'-dinonyl-2,2'-dipyridyl, 4,4',4"-tri-t-butyl-2,2':6',2"-terpyridine, 1,10-phenanthroline, 4,7-diphenyl-1,10-phenanthroline, silver nitrate, lithium perchlorate, lithium triflate, and nitrosonium tetrafluoroborate were purchased from Aldrich at ≧97% purity and used as received. 3-methoxypropionitrile (Aldrich 98%) and 4-(3-pentyl)pyridine (TCI 95+%) were distilled under dynamic vacuum prior to use. 4,4'-Dimethyl-2,2'-dipyridyl was purchased from Reilly Industries (Indianapolis, Ind.). 5,5'-Dimethyl-2,2'-dipyridyl, and 4,4',5,5'-tetramethyl-2,2'-dipyridyl were prepared using the procedure as described by Sasse et al., in *J. Am. Chem. Soc.* 1961, 83, 1347. All methyl-substituted bipyridines were recrystallized from ethyl acetate. 2,2'-Bipyridine-4,4'-dicarboxylic acid was prepared using the procedure as described by Nazeeruddin et al., in *Inorg. Synth.* 1997, 32, 181. 4,4',4"-Triethyl-2,2':6', 2"-terpyridine was prepared using the procedure as described by Nazeeruddin et al., in *J. Am. Chem. Soc.* 2001, 123, 1613. Cis-di(isothiocyanato)-bis(2,2'-bipyridine-4,4'-dicarboxylic acid)ruthenium(II) (i.e., "N3") was prepared using the procedure as described by Nazeeruddin et al., in *J. Am. Chem. Soc.* 1993, 115, 6382.

Example 1

This example illustrates a method for synthesizing 4,4'-di-(3-pentyl)-2,2'-dipyridyl.

Freshly distilled 4-(3-pentyl)pyridine (18 mL) was refluxed with 2 g of 10% Pd on activated carbon under nitrogen for 5 days. After cooling the mixture to room temperature, the solids were filtered and rinsed with dichloromethane ($CH_2Cl_2$). The solvent in filtrate was then removed by rotary evaporation. Most of the unreacted 4-(3-pentyl)pyridine was removed by vacuum distillation. The remaining viscous oil was subjected to flash column chromatography using silica gel. The eluent was a gradient of acetone in $CH_2Cl_2$ that was saturated with concentrated ammonium hydroxide solution. Combining and reducing the volume of the product containing fractions resulted in 2.7 g (16% yield) of 4,4'-di-(3-pentyl)-2,2'-dipyridyl in the form of a nearly colorless viscous oil that solidified into a waxy crystalline solid on standing at room temperature.

$^1$H NMR (300 MHz, CDCl$_3$) δ ppm: 0.81 (12H, t, 4×CH$_3$), 1.73 (8H, m, 4×CH$_2$), 2.50 (2H, m, 2×CH), 7.16 (2H, s, 2×H5), 8.34 (2H, s, 2×H3), 8.61 (2H, d, 2×H6).

Example 2

This example illustrates a method for synthesizing 2,2'-bipyridine-4,4'-dicarboxylic acid chloride.

Approximately 10 g of 2,2'-bipyridine-4,4'-dicarboxylic acid was placed in a 500 ml round-bottom flask fitted with a condenser. Thionyl chloride (ca. 200 ml) was added and the flask flushed with N$_2$. The solution was refluxed under a static N$_2$ atmosphere with stirring for three to four days. The solution was allowed to cool and the solids settle. Approximately 50 ml of the clear yellowish solution was decanted into a clean 250 ml flask being careful not to transfer any of the un-reacted solid. The thionyl chloride was removed by rotary evaporation leaving a slightly yellow-green solid on the sides of the flask. This product was used immediately without characterization or further purification.

Example 3

This example illustrates a method for synthesizing 2,2'-bipyridine-4,4'-di-t-butoxyester.

From a freshly opened bottle that had previously been warmed to melt the contents, ca. 20 ml of t-butyl alcohol was transferred to a clean dry Erlenmeyer flask. A piece of sodium (ca. 1 g) was washed several times with t-butyl alcohol and added to the Erlenmeyer flask. The flask was warmed with stirring under N$_2$ until the sodium had totally dissolved (ca. 1.5 hrs). This solution of sodium t-butoxide was then added to the flask containing the 2,2'-bipyridine-4,4'-dicarboxylic acid chloride. The flask immediately became hot to the touch. The resulting slurry was stirred for 30 min. and allowed to cool to room temperature. The solution was then filtered and the solid was washed with several portions of CH$_2$Cl$_2$.

The solution fractions were combined and the solvent removed by rotary evaporation leaving a yellowish solid on the sides of the flask. This solid consisted of the desired product, the monoacid-monoester bipyridine and a small amount of dicarboxylic acid bipyridine. The desired product was extracted from the solid mixture by adding several 10 ml portions of toluene to the flask and heating with swirling with a heat gun until the start of reflux. The toluene was then allowed to cool to room temperature before decanting from the solid residue. This processes was repeated until the toluene no longer tested significantly positive for dissolved bipyridine (by adding several drops to a solution of Fe(ClO$_4$)$_2$.X H$_2$O in acetone which turns red-purple if the product is present). The toluene fractions were combined, the volume reduced to a few milliliters, and the solution was placed in a freezer. White, waxy crystals formed and were filtered from the cold solution. The product thus obtained was pure by TLC (~1 g).

$^1$H NMR (300 MHz, CDCl$_3$) δ ppm: 1.65 (18H, s, 6×CH$_3$), 7.85 (2H, d, 2×H5), 8.84 (2H, m, 2×H3, 2×H6).

Example 4

This example illustrates a method for synthesizing 2,2'-bipyridine-4,4'-bis-(di-n-butylamide).

Approximately 20 ml of di-n-butylamine was added to a flask containing the 2,2'-bipyridine-4,4'-dicarboxylic acid chloride and the flask swirled for several minutes. After the reaction mixture cooled, approximately 100 ml of chloroform was added to the flask. This solution was extracted several times with aqueous NaOH. The organic layer was collected, dried with anhydrous sodium carbonate and reduced to a few milliliters. The crude product was chromatographed on silica gel using a gradient of acetone in CH$_2$Cl$_2$. The product obtained by removing the chromatography solvent was a white residue that had to be scraped from the sides of the flask. Estimated yield was ~1 g.

$^1$H NMR (300 MHz, CDCl$_3$) δ ppm: 0.81 (6H, t, 2×CH$_3$), 1.02 (6H, t, 2×CH$_3$), 1.15 (4H, two offset quintets, 2×CH$_2$), 1.43 (4H, two offset quintets, 2×CH$_2$), 1.52 (4H, p, 2×CH$_2$), 1.68 (4H, p, 2×CH$_2$), 3.20 (4H, t, 2×CH$_2$), 3.51 (4H, t, 2×CH$_2$), 7.30 (2H, m, 2×H5), 8.41 (2H, s, 2×H3), 8.74 (2H, m, 2×H6).

Example 5

This example illustrates a method for synthesizing [Co$^{II}$(L)$_3$]{ClO$_4$}$_2$ and [Co$^{II}$(L')$_2$]{ClO$_4$}$_2$ complexes.

All of the complexes depicted in FIG. 1 were synthesized using the same procedure. Briefly, 3 equivalents of a bidentate ligand or 2 equivalents of a tridentate ligand were dissolved with magnetic stirring in refluxing methanol. The volume of methanol was adjusted according to the solubility of the ligand and the scale of the reaction such that all of the ligand material was dissolved. To this mixture was then added 1 equivalent of cobalt(II) perchlorate hexahydrate and the mixture was allowed to stir at reflux for 2 hours. After cooling the mixture to room temperature, the total volume was reduced by ca. 80% using rotary evaporation. Addition of ethyl ether caused the precipitation of the product (as a solid that varied from light brown to light yellow), which was filtered and dried under vacuum. The resulting complexes were used without any further purification.

Example 6

This example illustrates a method for preparing a dye solution.

Saturated solutions of N3 were prepared by adding ca. 4 mg of dye to 10 ml of dry ethanol. This mixture was sonicated for ca. 10 minutes and filtered to remove undissolved dye.

Example 7

This example illustrates a method for preparing an electrode.

TiO$_2$ colloidal solutions were prepared either according to "Method A" reported by Nazeeruddin et al. (*J. Am. Chem. Soc.*, 1993, 115, 6382) or according to the method reported by Zaban et al. (*J. Phys. Chem. B*, 1997, 101, 55) and will be referred to as the nitric acid or acetic acid preparation, respectively. Films of the colloid were coated onto SnO$_2$:F coated glass electrodes (Pilkington TEC 15) using the "1 Scotch" method as described by Zaban et al. (*J. Phys. Chem. B*, 1997, 101, 55). After coating, the films were air-dried and then sintered in air at 450° C. for 1 hour. The still hot electrodes (ca. 80° C.) were then immersed in the dye solution and allowed to sit in the dark at least overnight. Photoanodes were kept in the dark and in the dye solution until needed. Just prior to use, they were removed from the dye solution, rinsed thoroughly with dry ethanol, and dried under a stream of nitrogen. In some cases, the photoanodes were further treated by immersing into a 0.5 M solution of 4-t-butylpyridine in acetonitrile (ACN) for 10–30 minutes followed by rinsing in ACN just prior to use.

Platinum-on-glass electrodes were made by a sputtering process. Gold-on-glass electrodes were made by thermal vapor deposition of 25 nm chromium followed by 150 nm gold on glass. Carbon-coated electrodes were made by spraying 3–5 coats of Aerodag G (Acheson) on $SnO_2$:F electrodes. The carbon coating produced in this way was very fragile, and each electrode was used in a cell once, as cell disassembly usually created large scratches in the carbon film.

Example 8

This example illustrates a method for preparing electron-transfer mediators.

Cobalt-based electron-transfer mediators were created by the addition of the desired Co(II) complex at various concentrations in either methoxypropionitrile (MPN) or γ-butyrolactone (gBL). In all cases, the appropriate amount of nitrosonium tetrafluoroborate ($NOBF_4$) was added to oxidize 10% of the added Co(II) complex. In some cases, 0.2 M 4-t-butylpyridine was added to the mediator solutions. Lithium triflate or $LiClO_4$ was also added at various concentrations to some mediator solutions. For the purposes of comparison, a standard iodide-based mediator solution was prepared that consisted of LiI and $I_2$ (10:1) in MPN.

Example 9

This example illustrates a method for measuring performance of electron-transfer mediators.

UV-vis spectra were obtained using a HP 8452A diode array spectrophotometer. A reduced volume, 1 cm path length, quartz cell was used for measurement of all solutions. Cyclic voltammetric data was obtained using a standard three-electrode cell with an EG&G PAR Model 173 Potentiostat/Galvanostat controlled by a Model 175 Universal Programmer. The data was recorded on a Yokogawa 3023 X-Y recorder. The reference electrode was $Ag/Ag^+$ (0.47 V vs. SHE) composed of 0.1 M silver nitrate in dimethylsulfoxide. The auxiliary electrode was a 0.5 $cm^2$ platinum flag and the working electrode was a glassy carbon ($7.1 \times 10^{-2}$ $cm^2$), gold ($7.1 \times 10^{-2}$ $cm^2$), or platinum ($2.8 \times 10^{-2}$ $cm^2$) disk electrode (BAS). Prior to use, each working electrode was polished on a felt pad with a water slurry of 0.3 µm alumina polishing powder, followed by rinsing and sonication in ACN. This polishing procedure was repeated before each electrochemical experiment. The supporting electrolyte was 0.1 M lithium perchlorate in ACN.

Photoaction spectra were obtained from DSSCs in a two-electrode sandwich cell arrangement. Typically 10 µl of electrolyte was sandwiched between a $TiO_2$ photoanode and a counter electrode. When solutions of the different cobalt mediators (0.25 M Co(II)/0.025 M $NOBF_4$) in MPN were used, the counter electrode was made of gold-sputtered on $SnO_2$:F-coated glass. A platinum-sputtered $SnO_2$:F-coated glass electrode was employed as a counter electrode when the redox mediator was 0.25 M LiI/0.025 M $I_2$. The cell was illuminated with a 150 W Xe lamp coupled to an Applied Photophysics high irradiance monochromator. The irradiated area was 0.5 $cm^2$. Light excitation was through the $SnO_2$:F-coated glass substrate of the photoanode. Photocurrents were measured under short circuit conditions with a Contron model DMM 4021 digital electrometer. Incident irradiance was measured with a calibrated silicon photodiode from UDT Technologies.

To test the performance of each electron-transfer mediator solution, cells were assembled by clamping together a photoanode and cathode in a cell holder having a light aperture area of 0.4 $cm^2$. The electron-transfer mediator was introduced by the addition of a few drops of solution at the edge of the electrodes. Capillary forces were sufficient to draw the solution onto the entire electrode area. Solar illumination was simulated using the output of an Oriel 75 W xenon arc lamp which was further attenuated using neutral density filters and a 400 nm high-pass cutoff filter. The light intensity after filtering was adjusted to 100 mW $cm^{-2}$ (ca. 1 sun) at the distance of the photoanode using a Molectron PowerMax 500A power meter. The current output of each cell was recorded in the dark and under solar illumination while sweeping the voltage between ca. 0.8 and −0.2 V using the same instrumentation as was used for cyclic voltammetry. The data thus obtained was digitized using an Acer flatbed scanner and tsEdit digitizing software on a computer running under Windows® 98.

Results and Discussion

Ligands

Cobalt complexes of tert-butyl substituted, in particular para-substituted, bipyridine or terpyridine ligands gave a quite good short circuit photocurrent densities ($J_{sc}$) and open circuit photovoltages ($V_{oc}$). It is believed that the difference in mediator behavior of t-butyl-substituted polypyridine ligands was related to the steric bulk of the t-butyl group. Three types of polypyridine ligands were examined: 2,2'-bipyridines, 1,10-phenanthrolines and 2,2':6',2"-terpyridines. Alkyl substituents having a range of steric requirements were examined. Since the electron-donating effect of all simple alkyl substituents is essentially the same (e.g., methyl, ethyl, t-butyl, etc., see Wade, L. G. *Organic Chemistry*; 2nd ed.; Prentice-Hall, Inc.: Englewood Cliffs, N.J., 1991; Chapter 17), all of the complexes of a given ligand-type (i.e., bipyridine, phenanthroline or terpyridine) were expected and found to have very similar $E_{1/2}$ values for the relevant Co(II/III) couple. In addition, several other types of bulky substituents were examined which have significantly different electronic effects. This group included aryl substituents and strongly electron-withdrawing ester and amide groups. These latter two types of substituents make the ligands electron-deficient and produce cobalt complexes with significantly more positive $E_{1/2}$ values; consequently, the maximum theoretically possible $V_{oc}$ is likewise greater. Hagfeldt et al., *Acc. Chem. Res.*, 2000, 33, 269.

Spectral Properties

All of the complexes under consideration exhibit similar UV-vis absorption spectra. Each of the Co(II) complexes has a weak absorption band centered at ca. 440–450 nm. The onset of the ligand-based π-π* transition occurs in the UV above 350–380 nm for each of the ligands. Molar extinction coefficients ($\epsilon_{\lambda max}$) for the band at 440–450 nm were obtained from Beer's law plots of standard solutions of each Co(II) complex. Table 1 summarizes the data for a set of representative complexes. The most intense visible absorption is for ttb-terpy$^{2+}$ with $\epsilon_{450}=1.4 \times 10^3$ $M^{-1}$ $cm^{-1}$. The remaining complexes all exhibit $\epsilon_{\lambda 440-450}$ values that are approximately an order of magnitude smaller. In all cases, the visible absorbance of the Co(III) form is almost imperceptible and partial oxidation of solutions of any of the Co(II) complexes reduces the overall absorbance. For the sake of comparison, the $\epsilon_{\lambda 440-450}$ value for $I_3^-$ is ca. $2 \times 10^3$ $M^{-1}$ $cm^{-1}$; therefore, except for ttb-terpy$^{2+}$ that has a comparable absorbance, considerably less visible light is absorbed by all of the remaining cobalt complexes at similar concentrations.

TABLE 1

Spectral properties of representative cobalt(II) complexes

| Complex | $\lambda_{max}$ (nm) | $\epsilon\lambda_{max}$ ($M^{-1}cm^{-1}$) |
|---|---|---|
| ttb-terpy | 450 | $1.4 \times 10^3$ |
| dtb-bpy | 440 | $1.4 \times 10^2$ |
| d3p-bpy | 440 | $1.1 \times 10^2$ |
| dn-bpy | 440 | $1.1 \times 10^2$ |
| bdb-amd | 440 | $1.5 \times 10^2$ |

Electrochemical Studies

Figure 2:
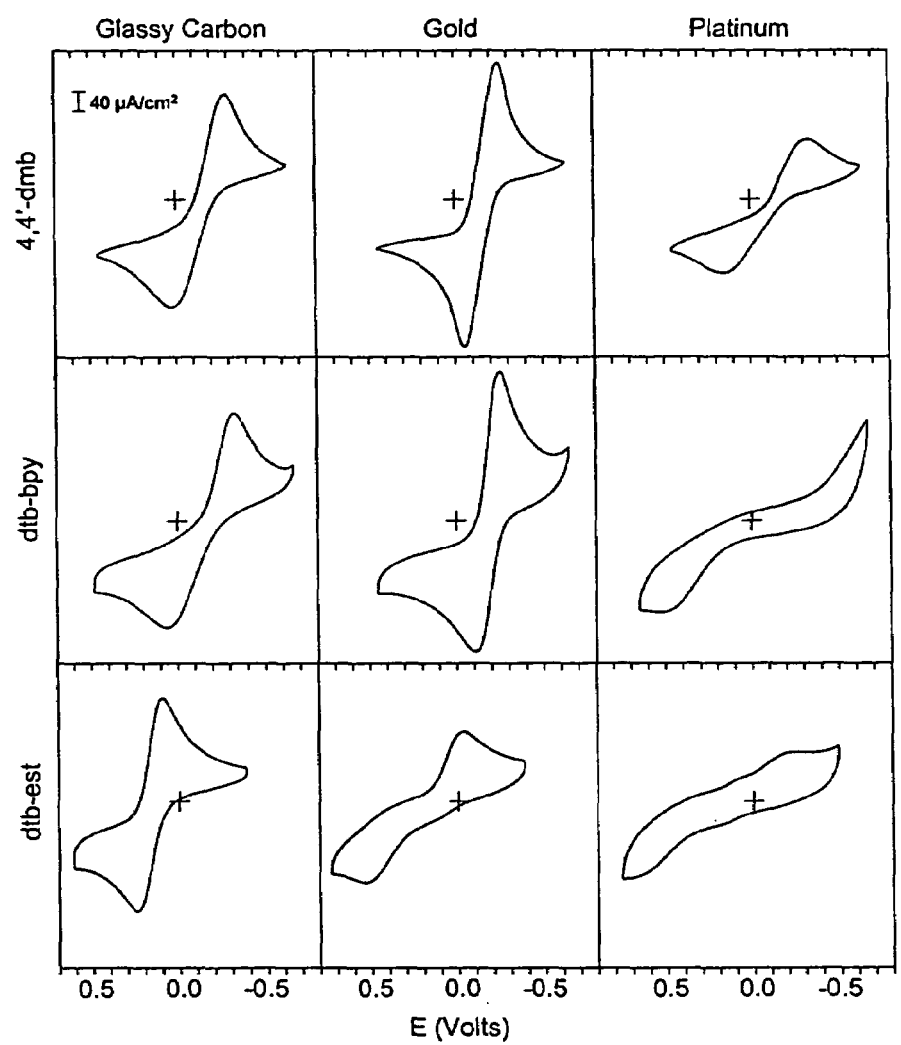
FIG. 2 shows cyclic voltammograms of three different cobalt complexes (in rows) on three different electrodes (in columns). The vertical axis is current density to compensate for modest differences in electrode areas, and the scale is indicated in the upper left hand corner. The concentration of the complexes was $10^{-3}$ M, and the scan rate was 200 mV s$^{-1}$.

Electrochemical characterization of these complexes revealed an electrode surface dependence to the electron-transfer kinetics. Each complex was examined by cyclic voltammetry on three different working electrodes: glassy carbon, gold, and platinum. FIG. 2 shows nine cyclic voltammograms (CVs) representing three different complexes (rows) on the three different working electrode surfaces (columns). The vertical axis in these CVs was converted to current density to normalize for the different electrode areas. Table 2 contains the measured electrochemical parameters for the complete set of complexes.

TABLE 2

Electrochemical properties of cobalt complexes

| | Glassy Carbon | | Gold | | Platinum | |
|---|---|---|---|---|---|---|
| Complex | $E_{1/2}$ (mV) | $\Delta E_P$ (mV) | $E_{1/2}$ (mV) | $\Delta E_P$ (mV) | $E_{1/2}$ (mV) | $\Delta E_P$ (mV) |
| te-terpy | −103 | 200 | −138 | 111 | −140 | 156 |
| ttb-terpy | −229 | 77 | −234 | 75 | (a) | (a) |
| bpy | −7 | 86 | −10 | 60 | −7 | 60 |
| 4,4'-dmb | −139 | 171 | −149 | 110 | −79 | 290 |
| 5,5'-dmb | −99 | 115 | −103 | 60 | −100 | 64 |
| tm-dmb | −217 | 123 | −225 | 57 | −141 | 326 |
| dtb-bpy | −139 | 271 | −177 | 86 | (a) | (a) |
| dp-bpy | −107 | 94 | −109 | 69 | −81 | 162 |
| d3p-bpy | −58 | 116 | −60 | 82 | (a) | (a) |
| dn-bpy | −147 | 80 | −143 | 76 | −125 | 221 |
| phen | 80 | 198 | 73 | 87 | 81 | 153 |
| phen-phen | −87 | 60 | −84 | 75 | −71 | 163 |
| dtb-est | 174 | 103 | 242 | 398 | 257 | 631 |
| bdb-amd | 217 | 101 | 222 | 86 | 291 | 442 |

(a) No discernable cathodic peak

The results found for 4,4'-dmb and dtb-bpy (FIG. 2, top and middle rows, respectively) are typical of complexes with ligands containing alkyl substituents in the 4 and 4' (or equivalent) positions. Of the three electrodes, gold electrodes exhibit the most reversible and ideally shaped CVs. Glassy carbon electrodes also produce quasi-reversible voltammograms, although less reversible than gold. Quite unexpectedly, the voltammetry on platinum electrodes is quite irreversible with large anodic and cathodic peak separations ($\Delta E_p$) or, in some cases, peaks that are so broad as to be indistinguishable as peaks. Of the metal-ligand complexes shown in FIG. 1, the voltammetry of the dtb-est complex (FIG. 1, bottom row), is most reversible on glassy carbon with $\Delta E_p$ increasing on gold and platinum.

Complexes whose ligands are either un-substituted or are substituted only in the 5 and 5' positions with methyl groups exhibited different behavior (see Table 2). In general, there is a less surface dependence. Gold and platinum electrodes give nearly reversible voltammograms while the CV's on glassy carbon are quasi-reversible.

In general, it is believed that the shapes of the quasi-reversible waves indicate that, in cases where the heterogeneous electron transfer is slow, the transfer coefficient, α, is considerably greater than 0.5. See Bard et al., *Electrochemical Methods*; $1^{st}$ ed.; John Wiley & Sons: New York, 1980; Chapter 3. In other words, it is believed that for equivalent overpotentials the heterogeneous reduction of the Co(II) complex is considerably faster than the corresponding oxidation of the Co(II) species. While the electrode-dependent electron-transfer kinetics are presently not fully understood, there is a rough empirical correlation between the solution voltammetry of a complex and its performance as a redox mediator in a DSSC. The complexes that exhibit reversible or nearly reversible voltammetry on all three electrodes (i.e., gold, platinum, and glassy-carbon) are generally poor mediators; i.e., they give low $J_{sc}$ values. The voltammetric results also suggest that, while platinum is the cathode of choice for the $I^-/I_3^-$ redox mediator, it may not be the optimal choice for cobalt complex-based mediators. Likewise, while carbon is a poor cathode with the $I^-/I_3^-$ redox mediator system, it may be acceptable for any of the cobalt systems considered here.

Initial Screening of Mediators

To qualitatively and quantitatively compare these cobalt complexes as mediators, DSSCs were assembled using identical photoanodes and cathodes. Due to the varying solubility of the complexes, the concentration of mediator in solution was kept low. This resulted in devices with less than optimal performance, but allowed for comparisons in cell performance as a function of mediator structure.

As with the electrochemical observations, there were distinct differences in cell performance based on the identity of the ligand substituents and in what positions they were located. Mediators based on phen, phen-phen, bpy, 5,5'-dmb, or tm-bpy yielded almost no photocurrent. Mediators composed of 4,4'-dmb and te-terpy resulted in a very modest photoeffect, but both $V_{oc}$ and $J_{sc}$ were very low. Both dtb-est and bdb-amd gave $V_{oc}$>0.55 V but $J_{sc}$ that were ca. <10% that of the best cobalt-based systems. The remaining complexes showed better promise as potential efficient electron-transfer mediators.

Solvents and Cathode Materials

In surveying a number of potential low volatility solvents, MPN and gBL were found to work well with all of the cobalt mediators. For any given concentration of mediator, gBL was generally a superior solvent, in that the fill factor (FF) was improved over the same cell made with MPN as the mediator solvent. However, in some cases the mediators were more soluble in MPN, and in those cases the higher concentration of mediator made for better cell performance.

Gold cathodes gave higher $J_{sc}$ than platinum since, for efficient mediators, the reduction of $Co(L)_3^{3+}$ (e.g. dtb-bpy$^{3+}$, FIG. 2) is much faster on gold than platinum. For all the efficient cobalt complex mediators, cells assembled using gold cathodes generally gave better performance than those assembled with platinum. However, platinum gave better results than might have been anticipated from the voltammetry. There was no evidence that the cobalt complexes were corrosive towards the gold surface. In fact, the same gold cathode was used throughout the course of these experiments, and remained substantially unchanged.

Based on the CV results, it is expected that a carbon cathode should also work well in these cells. Cathodes consisting of $SnO_2$:F glass coated with a thin layer of graphite nanoparticles were prepared. These carbon-coated cathodes worked well even outperforming platinum. In some instances, however, carbon-coated cathodes were not as stable for extended periods. In general, a stable carbon cathode functions well in cells based on electron-transfer mediators of the present invention.

Photoaction Spectra

Figure 3:
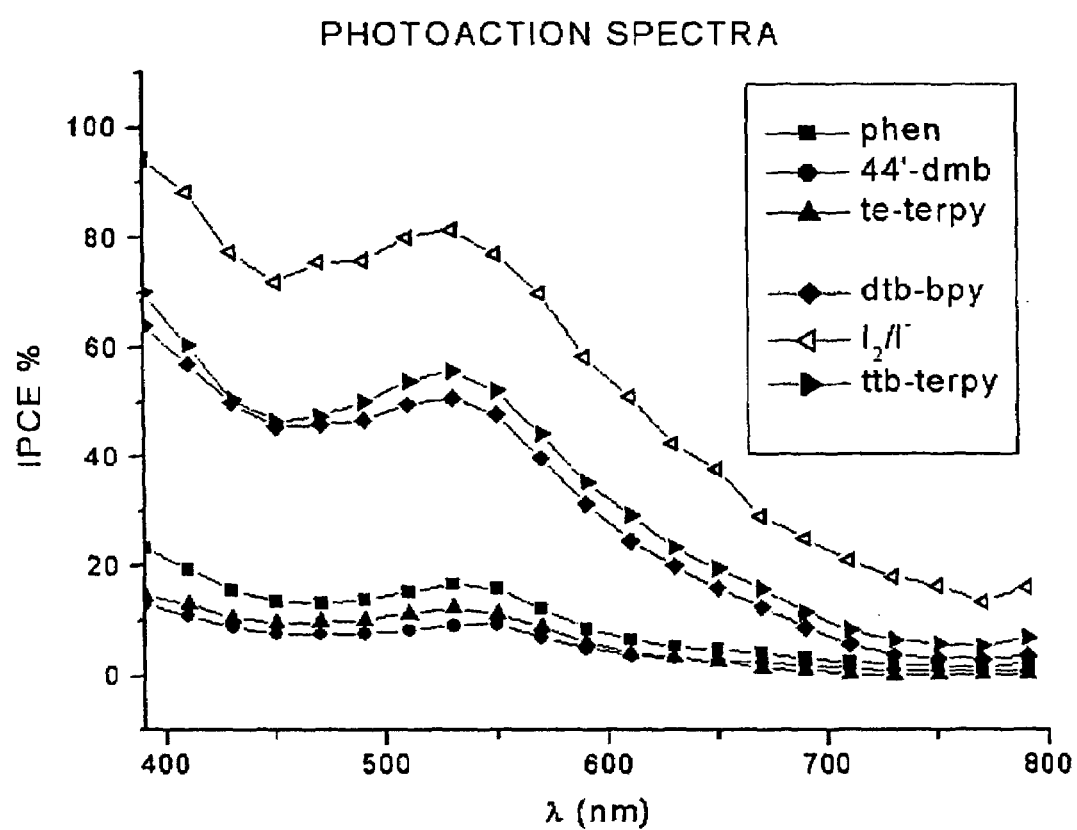
FIG. 3 is a photoaction spectra of N3 bound to nanocrystalline TiO$_2$ films in the presence of different electron mediators in MPN solutions: 0.25 M LiI/25 mM I$_2$ (—◁—), 0.25 M ttb-terpy$^{2+}$/25 mM NOBF$_4$ —▶—, 0.25 M dtb-bpy$^{2+}$/25 mM NOBF$_4$ (—◆—), 0.25 M phen$^{2+}$/25 mM NOBF$_4$ (—■—), 0.25 M te-terpy$^{2+}$/25 mM NOBF$_4$ (—▲—), saturated (<0.15 M) 4,4'-dmb$^{2+}$/15 mM NOBF$_4$ (—●—). 0.25 M LiClO$_4$ was added to all solutions containing a cobalt mediator.

Photoaction spectra-incident photon-to-current conversion efficiency (IPCE) versus wavelength—of N3 bound to nanocrystalline $TiO_2$ films in the presence of different electron-transfer mediators in MPN solutions are shown in FIG. 3. The performances of the photoelectrochemical cell are observed to be dependent on the composition of the electrolyte solution. A conversion efficiency of ca. 80%, in correspondence to the metal-to-ligand charge-transfer absorption maximum of N3 was obtained in the presence of 0.25 M LiI/0.025 M $I_2$. With the cobalt complex mediators, an excellent performances were observed when solutions of ttb-terpy$^{2+}$/ttb-terpy$^{3+}$ (ca. 55% IPCE) and dtb-bpy$^{2+}$/dtb-bpy$^{3+}$ (ca 50% IPCE) were used. In other cases, the phen, te-terpy, and 44'-dmb complex-based mediators exhibited maximum IPCE values in the range of 10–20%.

Open-Circuit Voltage

Figure 4:
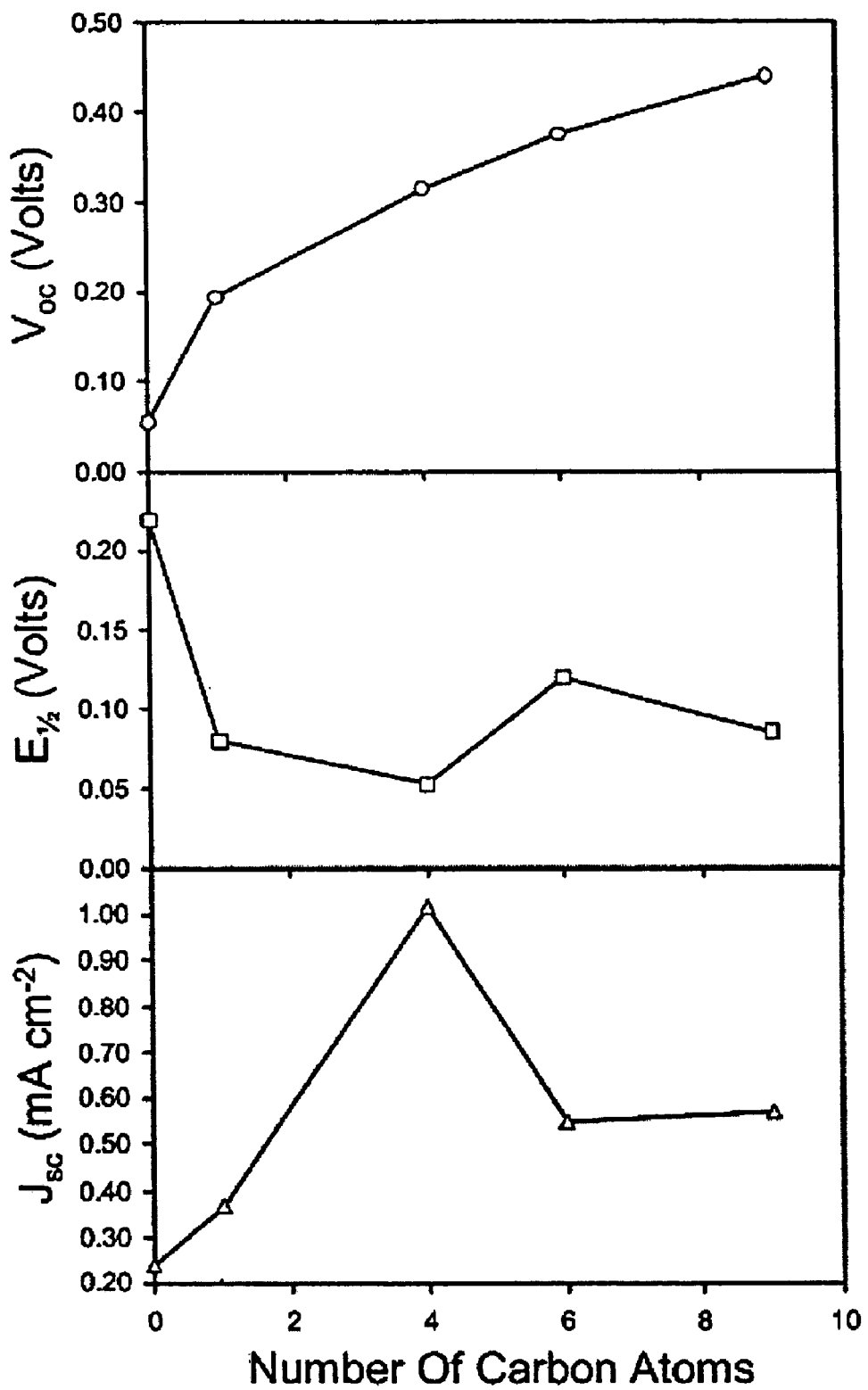
FIG. 4 is a plot of V$_{oc}$, E$_{1/2}$, and J$_{sc}$ as a function of the number of carbon atoms in the alkyl or aryl substituents at the 4 and 4' positions of 2,2'-bipyridine ligands. V$_{oc}$ and J$_{sc}$ were measured in DSSCs with a gold cathode and containing 125 mM Co(II)L$_3$ and 13 mM NOBF$_4$ in MPN.

FIG. 4 shows $V_{oc}$, $E_{1/2}$ and $J_{sc}$ data for five different cobalt bipyridine electron-transfer mediators plotted against the number of carbons in the substituents. In each case, the substituent is either an aryl or alkyl group that is appended at the 4 and 4' positions. These measurements were all made using MPN as the solvent. The mediators were all 125 mM in Co(II)L$_{31}$ and 13 mM in Co(III)L$_3$ and no other significant cations were present and the solution contained no pyridine type bases. As shown in FIG. 4, there is a steady increase in the value of $V_{oc}$ with the number of carbons in the ligand's substituents, which appears to be asymptotically approaching a limiting value. In the most generally accepted description, $V_{oc}$ is the difference of the quasi-Fermi level of electrons at the negative electrode and the "holes" at the positive electrode. See, for example, Hagfeldt et al., *Acc. Chem. Res.*, 2000, 33, 269; Cahen et al., *J. Phys. Chem. B*, 2000, 104, 2053; and Huang et al., *J. Phys. Chem. B*, 1997, 101, 2576. This latter term is essentially the Nerstian potential of the cobalt couple at the cathode. All of the 4,4'-alkyl and 4,4'-aryl substituted bipyridine complexes herein have similar $E_{1/2}$ (within ca. 60 mV), so it is expected that they will all yield approximately the same $V_{oc}$, all else being equal. The fact that $V_{oc}$ varies by ca. 400 mV over this collection of mediators indicates that something must shift the Fermi energy of the electrons in the $TiO_2$. Two of the most obvious candidates are shifts in the conduction band edge of the $TiO_2$ or differences in the rates of electron/Co(III)L$_3$ recombination. With I$^-$/I$_3^-$, numerous studies have demonstrated that $V_{oc}$ depends on the size of the countercation of iodide. See, for example, Kelly et al., *Langmuir*, 1999, 15, 7047; and Enright et al., *J. Phys. Chem.*, 1994, 98, 6195. This effect is ascribed to a shift in the conduction band edge energy of $TiO_2$ upon adsorption and/or intercalation of cations; and the magnitude of this shift is related to the charge-to-radius ratio of the cation. The complexes considered in FIG. 4 are of different sizes and the trend in $V_{oc}$ is in the correct direction to be consistent with this model (i.e., $V_{oc}$ increases with larger radius). Furthermore, Nusbaumer et al. (*J. Phys. Chem. B*, 2001, 105, 10461) have shown that a related cobalt complex-based mediator does adsorb on the $TiO_2$ surface. While this is generally in qualitative agreement with the model, it does not stand up to a more quantitative analysis. With I$^-$/I$_3^-$, the typical shift in $V_{oc}$ upon changing between Li$^+$ and Cs$^+$ is less than 200 mV (at comparable concentrations) while their ionic radii differ by almost a factor of ×3. Liu et al., *Sol. Energy Mater. Sol. Cells*, 1998, 55, 267. The difference in $V_{oc}$ between bpy and dn-bpy mediated cells is ca. 400 mV but their radii differ by, at most, a factor ×2. Thus, it is believed that the variations in $V_{oc}$ arise from differences in the recombination rate between Co(III)L$_3$ and photoinjected electrons, which is expected to decrease as the bulk of the substituents increases.

Lithium Ion Effect

As considered above, the presence of small countercations (most notably Li$^+$) in mediator solutions of I$^-$/I$_3^-$ lowers $V_{oc}$. Concomitantly, $J_{sc}$ increases, and the net result is an overall improvement in cell efficiency (η). Kelly et al., *Langmuir*, 1999, 15, 7047. There is ample experimental verification that adsorbed Li$^+$ lowers the energy of acceptor states in the $TiO_2$; and this fact is the most commonly invoked explanation for the cation-induced decrease in $V_{oc}$. Id. The origin of the increased $J_{sc}$ upon addition of Li$^+$ to the I$^-$/I$_3^-$ is less clear. Photoinjection of electrons from the excited dye occurs with near unity quantum efficiency irrespective of the cation. Since the photocurrent is determined by the difference between the photoinjection rate and the overall recombination rate, any increase in $J_{sc}$ must lie in cation-induced changes in recombination rates (irrespective of the type of mediator system).

In principle, Li$^+$ could decrease recombination in at least three ways: (1) by accelerating the rate of oxidized dye reduction by I$^-$, (2) by slowing the rate of direct combination of electrons with the dye or (3) it could slow the rate of recombination of electrons with I$_3^-$. Grätzel et al. (*J. Phys. Chem. B*, 2000, 104, 1791) showed that Li$^+$ (and other cations with high charge-to-radius ratios) greatly accelerate the rate of reaction between I$^-$ and adsorbed photooxidized N3. For the I$^-$/I$_3^-$ system this is largely irrelevant to $J_{sc}$ because, at usual I$^-$ concentrations, the rate of reaction between oxidized N3 and I$^-$ is fast even in the absence of Li$^+$. Id. Consequently, neither processes (1) nor (2) above is believed to be a significantly factor in determining $J_{sc}$. Thus, it is believed that the recombination reaction of electrons with I$_3^-$ is the dominant factor. The Li$^+$-induced lowering of the acceptor state energies in the $TiO_2$ could result in a driving-force-based decrease in the rate of I$_3^-$ reduction at the photoanode. Alternately, and most probably, adsorbed cations affect the rate and or mechanism of the heterogeneous electron transfer in some undetermined way.

Figure 5:
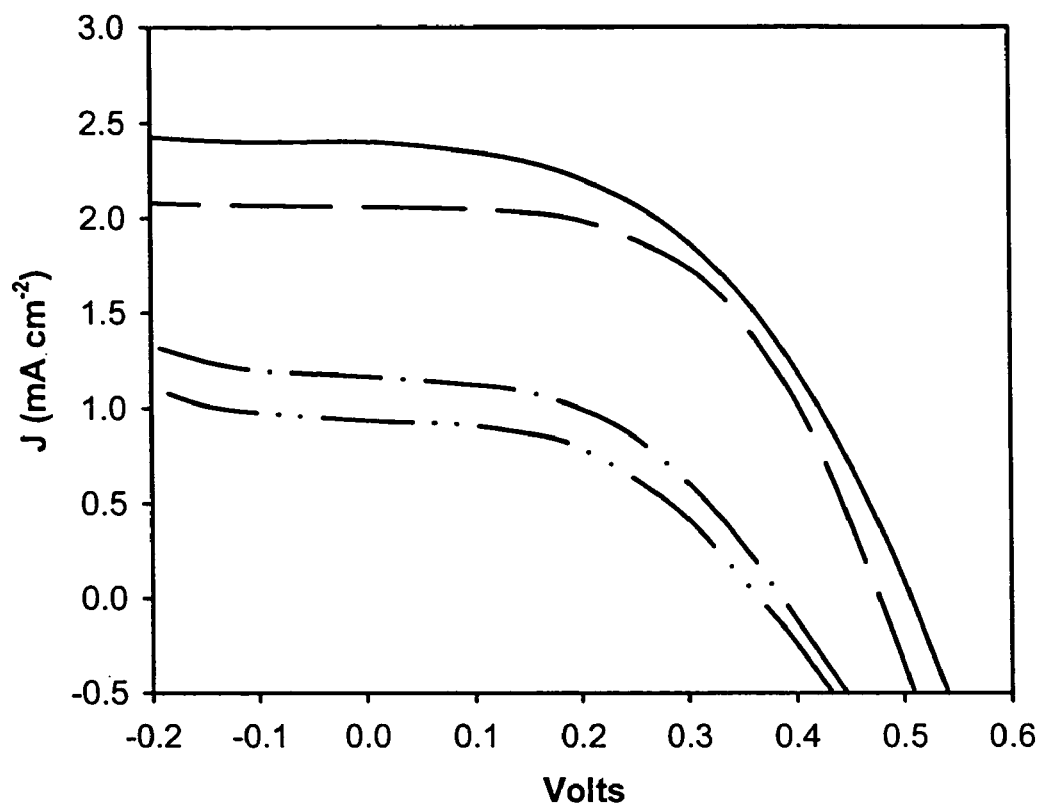
FIG. 5 shows current-voltage response of DSSCs with a gold cathode and containing: 0.25 M dtb-bpy and 25 mM NOBF$_4$ in gBL (-..-), with added 0.2 M 4-t-butylpyridine (-.-), with added 0.2 M 4-t-butylpyridine and 0.2 M lithium triflate (- -), and with added 0.2 M 4-t-butylpyridine and 0.5 M lithium triflate (-).

The addition of Li$^+$ to solutions of the cobalt-based mediators also increases $J_{sc}$ significantly, and FIG. 5 shows the current-voltage response of cells demonstrating this effect. The analogous three processes considered above remain relevant. As discussed in detail below in the discussion of $V_{oc}$, it is believed that Li$^+$ has a marked effect on the recombination rate with Co(III)L$_3$.

In contrast to I$^-$/I$_3^-$, Li$^+$ increases $V_{oc}$ with all of the efficient cobalt mediators. Since it is unlikely that the presence of the cobalt complex in solution would alter the effect of Li$^+$ in lowering the energy of the $TiO_2$ acceptor states (conduction band or surface states), it is believed that the Li$^+$-induced increase in $V_{oc}$ comes from some other source. This effect must be large enough to offset the band shift to lower energy. Li$^+$ has a negligible effect on the $E_{1/2}$ of the Co(II/III)L$_3$ couple at the cathode; thus, it is believed that such factor is not the origin of the increase in $V_{oc}$. Thus, as with the increase in $J_{sc}$, it is believed that factors directly tied to the recombination processes discussed above is responsible for the observed effect.

It is believed that the recombination reaction at the $SnO_2$:F contact is affected by $Li^+$. On a bare $SnO_2$:F electrode of the same type used as the $TiO_2$ current collector, the overpotential for dtb-bpy$^{3+}$ reduction is several hundred millivolts more negative in the presence of 0.25 M $Li^+$ and 0.10 M tetrabutylammonium ion ($TBA^+$) than in 0.10 M $TBA^+$ alone.

Pyridine Effect

The effect on $V_{oc}$ of adding 4-t-butylpyridine to a cobalt mediator solution parallels the behavior with the $I^-/I_3^-$ mediator system—a modest improvement results. As is evident from FIG. 5, there is also a small increase in $J_{sc}$ that is not typical of the $I^-/I_3^-$ mediator system. Huang et al., *J. Phys. Chem. B*, 1997, 101, 2576. When both 4-t-butylpyridine and $Li^+$ are present in solution, the increase in $V_{oc}$ is significantly greater than for either alone (see FIG. 5). The effect of added 4-t-butylpyridine on the energy of the conduction band and any other acceptor states in the $TiO_2$ is believed to be the same as with $I^-/I_3^-$. Additionally, the same effect was observed whether the 4-t-butylpyridine was added directly to the mediator solution or whether the photoanode was pre-treated by soaking in a solution of it.

*Chem.* 1991, 95, 30), thus it is believed that the process of mediation is diffusion controlled. Under high viscosity conditions, this diffusional transport of mediator between dye-sites and the cathode is hindered and thus may become the limiting factor in determining $J_{sc}$. This is consistent with the behavior observed, i.e., as the concentration of dn-bpy is increased, $J_{sc}$ first increases, then decreases. For cells containing a ttb-terpy-based mediator, similar behavior is observed, however, it is believed that the peaking of $J_{sc}$ values is due to the high $\epsilon_{\lambda max}$ observed for this complex—and since viscosity is not significantly different even at high concentrations of mediator.

Figure 6:
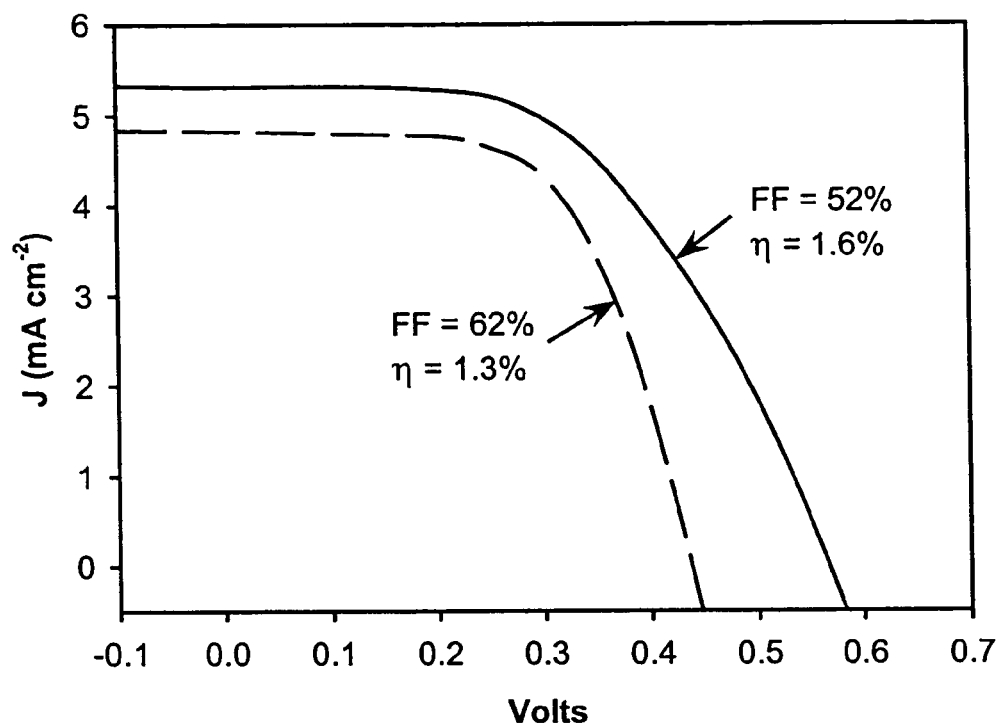
FIG. 6 shows current-voltage response of DSSCs assembled from N3-dyed photoanodes of acetic acid prepared TiO$_2$. These photoanodes were treated with a solution 0.5 M 4-t-butylpyridine in ACN just prior to use. The solid line represents a mediator of 0.5 M LiI and 50 mM I$_2$ in MPN using a platinum cathode. The dashed line represents a mediator of saturated (<0.5 M) dtb-bpy, 50 mM NOBF$_4$, and 0.5 M lithium triflate in gBL using a gold cathode.

Table 3 lists the data obtained for DSSCs fabricated using cobalt mediators and comparable $I^-/I_3^-$ mediators. All the cobalt complex mediated cells suffer from a $V_{oc}$ that is 100–200 mV less than the comparable $I^-/I_3^-$ mediated cells. Nonetheless, the performance of these cells is still quite good, and the $\eta$ relative to a comparable $I^-/I_3^-$ mediated cell ($\eta_{rel}$) is greater than 50% for d3p-bpy and dtb-bpy mediated cells. Cells containing the dtb-bpy-based mediators have exhibited an excellent performance, and FIG. 6 shows the current-voltage response of such a cell, which exhibits a FF of 62% and $\eta_{rel}$ of 82%.

TABLE 3

Photoelectrochemical properties of DSSCs containing cobalt complex-based mediators.

| Mediator[a] | Solvent | $V_{oc}$ (Volts) | $J_{sc}$ (mA cm$^{-2}$) | FF (%) | $\eta$[b] (%) | $\eta_{rel}$[c] (%) |
|---|---|---|---|---|---|---|
| 0.25 M dn-bpy, 0.25 M LiTriflate | gBL | 0.43 | 0.89 | 59 | 0.22 | 31 |
| 0.25 M dp-bpy, 0.2 M LiClO$_4$ | MPN | 0.40 | 0.97 | 49 | 0.19 | 27 |
| 0.25 M ttb-terpy, 0.5 M LiTriflate | MPN | 0.40 | 1.71 | 48 | 0.32 | 45 |
| 0.2 M d3p-bpy, 0.2 M LiClO$_4$ | MPN | 0.47 | 1.47 | 59 | 0.41 | 58 |
| 0.25 M dtb-bpy, 0.5 M LiTriflate | gBL | 0.51 | 2.40 | 47 | 0.57 | 80 |
| 0.25 M LiI, 0.03 M I$_2$ | MPN | 0.60 | 2.03 | 58 | 0.71 | — |
| Sat'd dtb-bpy, 0.5 M LiTriflate[d] | gBL | 0.44 | 4.82 | 62 | 1.30 | 82 |
| 0.5 M LiI, 0.05 M I$_2$[d] | MPN | 0.57 | 5.32 | 52 | 1.58 | — |

[a]The concentrations of complex given are for the total cobalt; each solution is 9:1 Co(II):Co(III). A gold cathode was used for all cells containing cobalt complex mediators; a platinum cathode was used in $I^-/I_3^-$ mediated cells. These mediator solutions also contained 0.2 M 4-t-butypyridine (see "d" below for exceptions).
[b]All efficiency measurements were carried out under 100 mW cm$^{-2}$ (~1 sun) illumination.
[c]This is the efficiency relative to a comparable $I^-/I_3^-$ mediated cell.
[d]The photoanodes in these cells were constructed with acetic acid prepared $TiO_2$, and after dyeing, were soaked in 0.2 M 4-t-butypyridine in ACN just prior to use.

Optimized Mediators

To fabricate DSSCs with higher $\eta$ and FF, the composition and concentration of the other mediators were surveyed. For dtb-bpy, d3p-bpy, and dp-bpy, it was found that good mediators were formed from saturated solutions of the corresponding Co(II) complexes and 0.5 M lithium triflate. The solubility limit in gBL at ambient temperature is less than 0.5 M for dtb-bpy and less than 0.3 M for d3p-bpy and dp-bpy in MPN. The oxidized form of these complexes are considerably less soluble than the corresponding Co(II) complexes under these conditions, and oxidation of 10% of the saturated solutions led to precipitation.

The dn-bpy and ttb-terpy-based electron-transfer mediators show an excellent performance at less than saturated concentrations. In some cases, above ca. 0.3 M, addition of more mediator actually lowers the $\eta$ of a cell. For dn-bpy, addition of the complex causes a significant increase in the viscosity of the solution. The self-exchange rates of cobalt complexes of this type are known to be slow (Szalda et al., *J. Phys. Chem.*, 1983, 22, 2372; and Newton, M. D. *J. Phys.*

Conclusions

Metal-ligand complexes of the present invention are excellent electron-transfer mediators for use in DSSCs. Cyclic voltammetric studies have shown a significant surface dependence of the electron-transfer kinetics. The electrochemical results showed that in some cases gold and carbon outperform platinum as cathode materials in these cells. Furthermore, these mediators show no tendency to be corrosive, enabling the use of metallized $SnO_2$:F electrodes required in large-area DSSCs.

Photoelectrochemical measurements of cobalt complex mediated cells revealed that in some cases addition of lithium salts improves their performance significantly. It is believed that the $Li^+$ effect observed with electron-transfer mediators of the present invention is due primarily to a reduction in the recombination rate between Co(III)L$_3$ and the electrons in $TiO_2$ and/or the $SnO_2$:F collector.

It is understood that the examples and embodiments described herein are for illustrative purposes only and that

What is claimed is:

1. A metal-ligand complex of the formula:

$L_a$-M wherein
a is 2;
M is cobalt; and
L is a ligand of the formula:

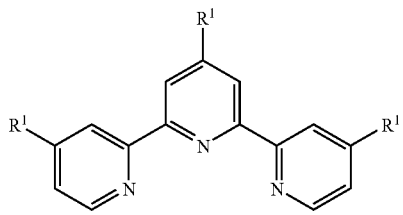

wherein each $R^1$ is independently alkyl, cycloalkyl, haloalkyl, heteroaryl, carboxy, or amide.

2. The metal-ligand complex according to claim 1, wherein each $R^1$ is independently alkyl.

3. The metal-ligand complex according to claim 2, wherein each $R^1$ is independently selected from the group consisting of ethyl and tert-butyl.

4. The metal-ligand complex according to claim 3, wherein $R^1$ is ethyl.

5. The metal-ligand complex according to claim 3, wherein $R^1$ is tert-butyl.

6. A dye-sensitized solar cell comprising:
a cathode;
a photoanode comprising a dye-sensitizer; and
an electron-transfer mediator operatively connected to said dye-sensitizer, wherein said electron-transfer mediator is a metal-ligand complex of the formula:

$L_a$-M-$X_b$ wherein
a is an integer from 1 to 6;
b is an integer from 0 to 5,
provided the sum of a and b equal the appropriate total number of ligands present on the metal M;
M is a transition metal;
each X is independently a co-ligand; and
each L is independently a substituted polypyridine ligand, wherein at least one of the substituent of the polypyridine ligand is other than a methyl group.

7. The dye-sensitized solar cell according to claim 6, wherein M is cobalt.

8. The dye-sensitized solar cell according to claim 6, wherein b is 0.

9. The dye-sensitized solar cell according to claim 8, wherein L is selected from the group consisting of a bidentate polypyridine, tridentate polypyridine, and a mixture thereof.

10. The dye-sensitized solar cell according to claim 9, wherein a is 2 or 3.

11. The dye-sensitized solar cell according to claim 10, wherein a is 2.

12. The dye-sensitized solar cell according to claim 11, wherein L is a tridentate polypyridine ligand of the formula:

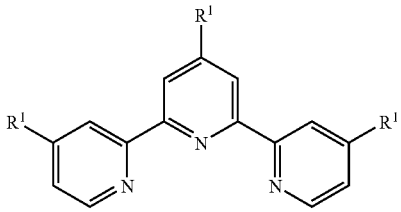

wherein each $R^1$ is independently hydrogen, alkyl, cycloalkyl, aryl, haloalkyl, hereroaryl, carboxy, or amide provided at least one $R^1$ is other than hydrogen or methyl.

13. The dye-sensitized solar cell according to claim 12, wherein each $R^1$ is independently hydrogen or alkyl.

14. The dye-sensitized solar cell according to claim 13, wherein each $R^1$ is independently selected from the group consisting of ethyl and tert-butyl.

15. The dye-sensitized solar cell according to claim 10, wherein a is 3.

16. The dye-sensitized solar cell according to claim 15, wherein L is a bidentate polypyridine ligand of the formula:

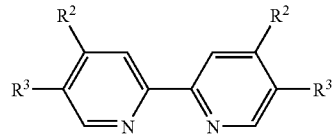

wherein each of $R^2$ and $R^3$ is independently hydrogen, alkyl, aryl, carboxy, amide, cycloalkyl, haloalkyl, or heteroaryl provided at least one of $R^2$ or $R^3$ is other than hydrogen or methyl.

17. The dye-sensitized solar cell according to claim 16, wherein each of $R^2$ independently selected from the group consisting of hydrogen, alkyl, aryl, carboxy, and amide.

18. The dye-sensitized solar cell according to claim 17, wherein each of $R^2$ is independently selected from the group consisting of hydrogen, alkyl, N,N-dialkyl amide, alkyl carboxy, phenyl, and haloalkyl.

19. The dye-sensitized solar cell according to claim 18, wherein each of $R^2$ is independently selected from the group consisting of hydrogen, methyl, tert-butyl, 3-pentyl, nonyl, N,N-dibutyl amide, tert-butyl carboxy, phenyl, and haloalkyl.

20. The dye-sensitized solar cell according to claim 15, wherein L is a bidentate polypyridine ligand of the formula:

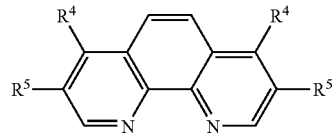

wherein each or $R^4$ and $R^5$ is independently hydrogen, alkyl, aryl, carboxy, amide, cycloalkyl, haloalkyl, or heteroaryl provided at least one $R^4$ or $R^5$ is other than hydrogen or methyl.

21. The dye-sensitized solar cell according to claim 20, wherein at least one of $R^4$ is aryl.

22. The dye-sensitized solar cell according to claim 21, wherein at least one of $R^4$ is phenyl.

23. The dye-sensitized solar cell according to claim 22, wherein $R^5$ is hydrogen.

24. The dye-sensitized solar cell of claim 6, wherein the electron-transfer mediator comprises a transition metal-polypyridine ligand complex selected from a moiety of the formula:

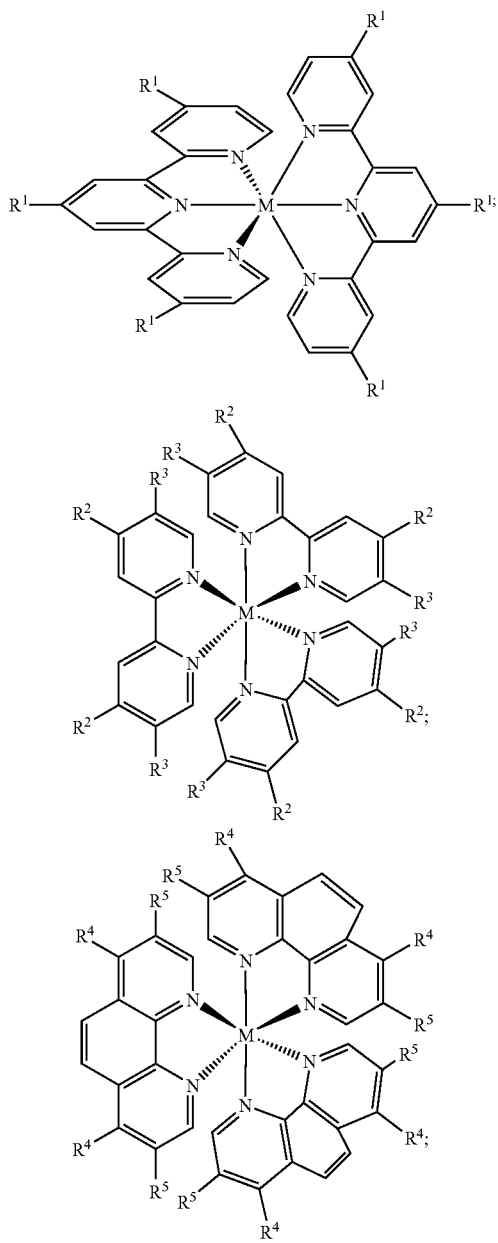

and a mixture thereof, wherein

M is a transition metal;

each $R^1$ is independently alkyl;

each of $R^2$, $R^3$, $R^4$, and $R^5$ is independently hydrogen, alkyl, aryl, carboxy, amide, cycloalkyl, heteroaryl, or haloalkyl provided at least one of ($R^2$ or $R^3$) and ($R^4$ or $R^5$) are other than hydrogen or methyl.

25. The dye-sensitized solar cell of claim 24, wherein M is cobalt.

26. The dye-sensitized solar cell of claim 24 further comprising a lithium salt.

27. A battery comprising a solar cell, a photoanode comprising a dye-sensitizer, and an electron-transfer mediator, wherein said electron-transfer mediator is a metal-ligand complex of the formula:

$$L_a\text{-}M\text{-}X_b$$

wherein a is an integer from 1 to 6;

b is an integer from 0 to 5, provided the sum of a and b equal the appropriate total number of ligands present on the metal M;

M is a transition metal;

each X is independently a co-ligand; and each L is independently a substituted polypyridine ligand, wherein at least one of the substituent of the polypyridine ligand is other than a methyl group.

28. A photoelectrochromic device comprising a dye and an electron-transfer mediator, wherein said electron-transfer mediator is a metal-ligand complex of the formula:

$$L_a\text{-}M\text{-}X_b$$

wherein a is an integer from 1 to 6;

b is an integer from 0 to 5, provided the sum of a and b equal the appropriate total number of ligands present on the metal M;

M is a transition metal;

each X is independently a co-ligand; and each L is independently a substituted polypyridine ligand, wherein at least one of the substituent of the polypyridine ligand is other than a methyl group.

* * * * *